United States Patent [19]
Reid et al.

[11] Patent Number: 5,576,207
[45] Date of Patent: Nov. 19, 1996

[54] METHOD OF EXPANDING HEPATIC PRECURSOR CELLS

[75] Inventors: Lola M. Reid, Chapel Hill, N.C.; Maria Agelli, Summit, N.J.; Andreas Ochs, Bronx, N.Y.

[73] Assignee: Albert Einstein College of Medicine of Yeshiva University, a Division of Yeshiva University, Bronx, N.Y.

[21] Appl. No.: 265,696

[22] Filed: Jun. 24, 1994

Related U.S. Application Data

[63] Continuation of Ser. No. 741,128, Aug. 7, 1991, abandoned.

[51] Int. Cl.$^6$ .............................. C12N 5/00; C12N 5/06; C12N 5/08
[52] U.S. Cl. .................... 435/240.2; 435/240.21; 435/240.23
[58] Field of Search ........................ 435/240.2, 240.21, 435/240.23

[56] References Cited

U.S. PATENT DOCUMENTS 5,030,105   7/1991   Kuri-Harcuch et al. ................. 435/29

OTHER PUBLICATIONS

Tsai, et al "Isolation of a human stromal cell strain secreting hemopoietic growth factors" Biol. Abstracts #22,434 83(2) 1986.

Hirata et al, "Effects of basement membrane matrix on the culture of fetal mouse hepatocytes" Biological Abstracts 57,933 77(8) 1983.

Maurer in *Animal Cell Culture,* Ed. by R. I. Freshney p. 23, 1986.

Enat et al. 1984. PNAS USA 81:1411–5.

*Primary Examiner*—Stephen G. Walsh
*Assistant Examiner*—Elizabeth C. Kemmerer
*Attorney, Agent, or Firm*—Amster, Rothstein & Ebenstein

[57] ABSTRACT

A composition which comprises an animal cell population, and which contains immature animal cells. The immature animal cells are characterized by expression of alpha-fetoprotein or lack of essential expression of alpha-fetoprotein and albumin, and at least a portion of said immature animal cells or at least a portion of the progeny of said immature cells is capable of differentiating into cells which express albumin. The cell population is cultured under conditions which result in expansion of the cells. Expansion of the cells may be achieved by culturing the cells in the presence of an extracellular matrix and liver stromal cells; and preferably in the presence of growth factors. Such cells may be used for liver transplantation, artificial livers, and for toxicology and pharmacology studies. Such cells may also be genetically engineered to express proteins or polypeptides of interest.

13 Claims, No Drawings

METHOD OF EXPANDING HEPATIC PRECURSOR CELLS

This is a continuation of application(s) Ser. No. 07/741,128 filed on Aug. 7, 1991, now abandoned.

This invention relates to the expansion, or proliferation of cells and in particular cells whose progeny may differentiate into mature hepatocytes. More particularly, this invention relates to the enrichment of, and to the expansion or proliferation of such cells in the presence of stromal cells, an extracellular matrix, and/or growth factors. In another aspect, this invention relates to genetically engineered cells which are capable of differentiating into hepatocytes.

In accordance with an aspect of the present invention, there is provided a composition which comprises an animal cell population. The cell population contains immature cells (i) at least a portion of said cells or a portion of the progeny of said cells is capable of differentiating into hepatocytes and (ii) which are characterized by expression of alpha-fetoprotein or lack of essential expression of alpha-fetoprotein and albumin, and at least a portion of said cells or of the progeny of said cells is capable of differentating into cells which express albumin. In general, the differentiated cells which express albumin have morphological and physiological characteristics of mature hepatocytes. The cell population has been cultured under conditions which result in expansion of the immature cells. Such cells are sometimes hereinafter referred to as "hepatocyte precursors".

The hepatocyte precursors may be derived from any animal, preferably from mammals. Mammals from which the hepatocyte precursors may be derived include, but are not limited to, humans, rodents (e.g., rats, mice, hamsters), rabbits, bovines, horses, pigs, and sheep. Preferably, the hepatocyte precursors are derived from humans.

Although the hepatocyte precursors are preferably obtained from liver tissue, such cells may be obtained from other sources, such as, but not limited to, the pancreas, gut, lung, and bone marrow.

In general, such hepatocyte precursors may be obtained from an excised section of liver. The excised section of liver may then be dissociated by standard procedures into single dissociated cells. Such procedures include enzymatic dissociation and mechanical dissociation. Enzymatic dissociation may be carried out in the presence of protease(s), such as collagenase(s) and/or nuclease(s), such as DNase. In some instances, pronase(s) may also be used. Such pronase(s) also contribute to the enrichment of hepatocyte precursors. An example of enzymatic dissociation of liver cells is described in Pretlow, et al., eds., *Cell Separation: Methods and Selected Applications*, pgs. 45–77, Academic Press, New York (1987). The cells are then subjected to an enrichment procedure to eliminate mature liver cells from the cell population. Various procedures exist for enrichment. Such procedures include, but are not limited to, enzymatic digestion with pronase, DNase, and collagenase; centrifugal elutriation for cells which are smaller than mature hepatocytes; and freezing the cells in liquid nitrogen in the presence of 10% glycerol. It is to be understood, however, that the scope of the present invention is not to be limited to cells of a specific size range or a specific morphology.

Alternatively, the immature cells may be enriched by contacting cells from an excised section of liver tissue, or of other tissue, which may contain the hepatocyte precursor cells, with monoclonal antibodies which recognize an epitope of the hepatocyte precursor cells. Such cells may then be separated from the remainder of the cells of the excised tissue by procedures known to those skilled in the art.

One example of an enrichment procedure entails obtaining a liver section, and placing the liver section in an ice-cold saline solution which may contain buffers, glucose, and/or antibiotics. The liver section is then minced and sequentially digested with a solution containing collagenase, pronase, and deoxyribonuclease, prepared in a saline solution to which $CaCl_2$ is added. The digestions preferably are done at 37° C. in a shaking water bath and for a period of time of about 20 minutes. The partially digested tissue is then strained through a tissue sieve by gravity and the undigested remnants are redigested two times as hereinabove described. The collected cells are then washed with saline solution, counted, and assessed for viability.

The enriched hepatocyte precursor population may then be cultured under conditions which result in the expansion, or proliferation of the hepatocyte precursors. Thus, in accordance with another aspect of the present invention, there is provided a process for expanding, or proliferating immature cells characterized as hereinabove described. The process comprises culturing the immature cells under conditions providing for expansion of the immature cells. Preferably, the process comprises culturing the immature cells in the presence of (i) an extracellular matrix and (ii) liver stromal cells. Preferably, the liver stromal cells are embryonic liver stromal cells or fetal liver stromal cells. In general, stromal cells are mesenchymally-derived cells that in vivo are closely associated with and are in a paracrine relationship with epithelia. Stromal cells also grow readily in culture on tissue culture plastic and in serum-supplemented media. In general, such cells also produce fibrillar collagens.

The term "expanding", as used herein, means that the immature cells, or hepatocyte precursors, are cultured under conditions which result in the growth or proliferation of the immature cells.

Examples of extracellular matrix components include, but are not limited to collagen, such as, for example, collagen Type IV, or the adhesion proteins fibronectin, and laminin. A preferred extracellular matrix component is collagen Type IV. The collagen, when employed, may be used alone or in combination with laminin or fibronectin, or in combination with proteoglycans, or with tissue extracts enriched in extracellular matrix materials.

Preferably, the extracellular matrix component is coated upon a porous solid support. Examples of porous solid supports which may be employed include, but are not limited to porous supports such as Millicell membrane supports, filters, sponges, and hollow fiber systems. Alternatively, the extracellular matrix may be unattached to the porous solid support. Examples of such matrices include floating collagen gels, gel foams, spheres of synthetic materials or fibers of synthetic materials such as dextran, polystyrene, and agarose.

The hepatocyte precursors are cultured in a suitable basal medium, preferably a serum-free medium. More preferably, the medium has a calcium content of less than 0.4 mM. Examples of such media include, but are not limited to, Ham's F10, Ham's F12, and RPMI 1640. In a preferred embodiment, the basal medium may further include at least one growth factor. Growth factors which may be employed include, but are not limited to, interleukins, such as interleukin-1 and interleukin-3; fibroblast growth factors; prolactin; growth hormone; transforming growth factors such as transforming growth factor-α; insulin-like growth factors, such as IGF-I and IGF-II; glucagon; insulin; platelet-derived growth factor; thyroid hormones, such as T3; hepatopoietins such as hepatopoietin A and hepatopoietin B; epidermal growth factors (EGF); dexamethasone; norepinephrine; and transferrin. One or more of such growth factors may be contained in a serum-free medium referred to as hormonally-defined medium, or HDM. An example of HDM is further described in Enat, et al., *Proc. Nat. Acad. Sci.*, Vol. 81, pgs. 1411–1415 (1984). Representative examples of hormonally defined medium (HDM), which may be prepared in RPMI 1640, Ham's F10, Ham's F12, or other basal media, include the following components in the following concentrations:

| Component | HDM Concentration |
| --- | --- |
| Insulin | 10 µg/ml |
| Growth hormone | 10 µU/ml |
| Prolactin | 20 mU/ml |
| Glucagon | 10 µg/ml |
| EGF | 50 ng/ml |
| Dexamethasone | $10^{-8}$ M |
| T3 | $10^{-9}$ M |
| Selenium | $3 \times 10^{-10}$ M |
| Copper | $10^{-7}$ M |
| Zinc | $10^{-10}$ M |

The basal medium may further include a supplement such as, for example, bovine serum albumin, lipoproteins such as high density lipoproteins (HDL), and/or free fatty acids. Free fatty acids which may be contained in the supplement include, but are not limited to, palmitic acid, palmitoleic acid, stearic acid, oleic acid, linoleic acid, and linolenic acid, or mixtures thereof.

An example of a medium which contains such supplements contains Ham's F12 medium to which is added 0.4% bovine serum albumin, and 76 mEq per liter of a free fatty acid mixture having the following free fatty acids in the following proportions:

| Palmitic acid | 31% |
| --- | --- |
| Palmitoleic acid | 2.8% |
| Stearic acid | 11.6% |
| Oleic acid | 13.4% |
| Linoleic acid | 35.6% |
| Linolenic acid | 5.6% |

Such medium is sometimes hereinafter referred to as medium HBF.

As a further representative example, either Ham's F12 medium or medium HBF may include the following growth factors, hormones, or other chemicals used as supplements in the concentrations given below:

| Component | Concentration |
| --- | --- |
| Dexamethasone | $10^{-6}$ M |
| Insulin | 0.1 to 100 µg/ml |
| Multi-Stimulating activity (MSA)* | 50 ng/ml |
| EGF | 25 to 100 ng/ml |
| Norepinephrine | $10^{-4}$ M |
| Hepatopoietins | 25 µl/ml |
| FGF's | 10 ng/ml |

*Obtained from Sigma Chemical Co., St. Louis, Mo. MSA contains insulin-like growth factor-I and insulin-like growth factor-II.

The number of such immature cells cultured under conditions such as those hereinabove described may be monitored by a variety of procedures. In general, the number of such cultured immature cells can increase by at least about 3-fold in a period of one week, preferably at least about 10-fold.

In one preferred embodiment, a human liver cell population, which has been enriched for hepatocyte precursors, is plated on or in a matrix of collagen Type IV under conditions in which the cells could polarize and feed through a basal surface such as a Millicell support. The matrix-bound hepatocyte precursors would be provided with an embryonic liver-derived stromal cell feeder layer. The cells are cultured in a serum-free medium having less than 0.4 mM calcium, and rich in free fatty acids. Some expansion of the hepatocyte precursors occurs under such conditions. If one desires to accelerate the expansion of the hepatocyte precursors, one may add growth factors to the medium. Extensive growth, or expansion may be obtained by adding cytokines such as interleukin-3 or interleukin-1 to the medium. The addition of growth factors such as, for example, epithelial growth factor (EGF), fibroblast growth factor (FGF), or IGF-II induces the expansion of a higher proportion of hepatocyte precursors.

Although Applicants have disclosed herein examples of preferred embodiments for the expansion of the immature cells, it is also contemplated that within the scope of the present invention, other methods may be employed for the expansion of such cells.

Applicants have found that by growing hepatocyte precursors in a medium which contains liver stromal cells and an extracellular matrix, one is able to support, or expand or proliferate the hepatocyte precursors. One may obtain growth en masse of the cells (i.e., diffuse, proliferative growth), or in some cases, the growth of colonies of such immature cells, also known as clonal growth, as well as enabling the cells to survive for extended periods of time.

Upon expansion of the hepatocyte precursors, such expanded hepatocyte precursors may be cultured under conditions which enable at least a portion of the hepatocyte precursors or at least a portion of the progeny of such hepatocyte precursors to differentiate into mature hepatocytes; alternatively, such expanded hepatocyte precursors may be transplanted into a patient, preferably within the liver tissue, whereupon at least a portion of the hepatocyte precursors or a portion of the progeny of such hepatocyte precursors will differentiate into mature hepatocytes.

It is also contemplated that within the scope of the present invention, such hepatocyte precursors may be genetically engineered to express any of a wide variety of proteins or polypeptides.

Gene(s) of interest which may be expressed by the hepatocyte precursors, or the differentiated cells derived therefrom, include, but are not limited to: (1) gene(s) present in and expressed at biologically effective levels by normal liver cells, but present in and expressed in less than normal quantities in the liver cells of animals or human patients to be treated prior to transfer of gene(s) of interest into them; (2) gene(s) not expressed in normal mature liver cells; or (3) gene(s) expressed in normal mature liver cells but whose structure is defective in the animals or patients to be treated, leading to the production of a non-functional protein, alone or in any combination thereof.

The gene(s) of interest can be incorporated into the cellular genetic material (e.g., into genomic DNA) or can be present extrachromosomally (i.e., the gene persists as part of an episome and is expressed from the episome). The genetic material of interest can be DNA or RNA; the DNA can constitute all or a portion of a gene of interest (i.e., one whose expression in mature liver cells is desired).

The gene(s) incorporated into and expressed by the hepatocyte precursors or the differentiated cells dervied therefrom can additionally include genetic material (e.g., DNA) encoding a selectable marker, which provides a means by which cells expressing the gene(s) of interest can be identified and selected. Hepatocyte precursors containing incorporated genetic material (i.e., gene(s) of interest and, optionally, genetic material encoding a selectable marker) are referred to as transduced hepatocyte precursors or genetically engineered hepatocyte precursors.

The gene(s) can be introduced, by means of an appropriate vector, into isolated and/or cultured hepatocyte precursors, which are subsequently transplanted into the recipient. Alternatively, a vector which recognizes a hepatocyte precursor as a target may be injected into the recipient, whereby the vector is incorporated into the hepatocyte precursors.

Such hepatocyte precursors to be genetically modified ex vivo can be obtained from a human or non-human animal, modified and returned to the same human or non-human animal by transplanting or grafting or, alternatively, can be obtained from a donor (i.e., a source other than the ultimate recipient), modified and placed into a recipient, again by transplanting or grafting.

The genetically engineered cells of the present invention may be employed in treating any disease which results from a single gene defect which can be corrected by expression of the normal gene in the hepatocyte precursors or the differntiated cells derived therefrom. Genetically engineered cells of the present invention may be used, for example, for the delivery of polypeptides or proteins which are useful in prevention and therapy of an acquired or an inherited defect in hepatocyte (liver) function. For example, they can be used to correct an inherited deficiency of the low density lipoprotein (LDL) receptor, and/or to correct an inherited deficiency of ornithine transcarbamylase (OTC), which results in congenital hyperammonemia.

Such genetically engineered cells may also be employed in the treatment of hemophilia due to Factor VIII or Factor IX deficiency; alpha-1 anti-trypsin deficiency; phenylketonuria (PKU) or other illnesses resulting from defects in the urea cycle or other defects in metabolic pathways.

The genetically engineered hepatocyte precursors can be used to provide a desired therapeutic protein or peptide by a means essentially the same as that by which the protein or peptide is normally produced and, in the case of autologous grafting, with little risk of an immune response and graft rejection. In addition, there is no need for extensive (and often costly) purification of a polypeptide before it is administered to an individual, as is generally necessary with an isolated polypeptide. Such genetically engineered hepatocyte precursors produce the polypeptide as it would normally be produced.

Retroviral vectors may be used to transduce hepatocyte precursors with genetic material which includes gene(s) encoding polypeptide(s) or protein(s) of interest and/or genetic material encoding a dominant selectable marker.

Because genes can be introduced into hepatocyte precursors using a retroviral vector, they can be under (subject to) the retroviral vector control; in such a case, the gene of interest is transcribed from a retroviral promoter. A promoter is a specific nucleotide sequence recognized by RNA polymerase molecules that start RNA synthesis. Alternatively, retroviral vectors having additional promoter and regulatory elements (in addition to the promoter which is responsible for normal retroviral gene transcription), which are responsible for the transcription of the gene(s) of interest, can be used. This category includes, but is not limited to, promoters, enhancers, or other regulatory elements for genes normally expressed in the liver. For example, a construct in which there is an additional promoter modulated by an external factor or signal can be used, making it possible to control the level of polypeptide being produced by the modified hepatocyte precursors, or by mature hepatocytes which have differentiated from such precursors, by providing that external factor or signal. For example, heat shock proteins are proteins encoded by genes in which the promoter is regulated by temperature. In another example, the promoter of the gene which encodes the metal-containing protein metallothionine is responsive to cadmium (Cd) ions. Additional examples include promoters known to be responsive to cyclic AMP, or to glucocorticoids, or to interferons. Incorporation of these promoters or other promoters influenced by external signals also makes it possible to regulate the production of the polypeptide by the genetically engineered hepatocyte precursors or mature hepatocytes differentiated from such precursors.

It is also possible to use viruses other than retroviruses to genetically engineer or modify hepatocyte precursors. Gene(s) of interest can be introduced by means of any virus, or a vector derivative thereof which can express such gene(s) in such cells. For example, SV40, herpes virus, adenovirus, adeno-associated virus, Epstein-Barr virus, and papilloma virus can be used for this purpose. DNA viruses or their vector derivatives can also be used to introduce gene(s) of interest, as well as a gene encoding a selectable marker, into such immature cells.

It is also contemplated that the hepatocyte precursors may be transduced with non-viral expression vehicles or DNA constructs, such as plasmids, for example.

Hepatocyte precursors expressing the gene(s) of interest may be grown in tissue culture vessels; removed from the culture vessel; and introduced into the body. This can be done surgically, for example. In this case, the tissue which is made up of transduced hepatocyte precursors capable of expressing the nucleotide sequence of interest is grafted or transplanted into the body. For example, it can be placed in the abdominal cavity in contact with/grafted onto the liver or in close proximity to the liver. Alternatively, the genetically engineered hepatocyte precursors can be attached to a support, such as, for example, microcarrier beads, which are introduced (e.g., by injection) into the peritoneal space of the recipient. Direct injection of genetically engineered hepatocyte precursors into the liver or other sites is also contemplated. Alternatively, the genetically engineered hepatocyte precursors may be injected into the portal venous system or may be injected intrasplenically. Subsequent to the injection of such cells into the spleen, the cells may be transported by the circulatory system to the liver. Once in the liver such cells may express the gene(s) of interest and/or differentiate into mature hepatocytes which express the gene(s) of interest.

Once introduced into the body of an individual, a portion of the genetically engineered hepatocyte precursors or a portion of their progeny differentiates into mature hepatocytes, which provide a continuous supply of the protein, polypeptide, hormone, enzyme, or drug encoded by the gene(s) of interest. It is contemplated that such proteins, polypeptides or hormones may also be supplied by the hepatocyte precursors prior to, or in the absence of differentiation into mature hepatocytes. The amount of the protein, polypeptide, hormone, enzyme, or drug supplied in this way can be modified or regulated as needed.

Thus, the hepatocyte precursors are genetically engineered in such a manner that they produce a gene product (e.g., a polypeptide or a protein) of interest in biologically significant amounts. The hepatocyte precursors or the mature hepatocyte progeny therefrom, formed in this way can serve as a continuous drug delivery system to replace present regimens, which require periodic administration (by ingestion, injection, etc.) of the needed substance.

Genetically engineered hepatocyte precursors may be employed in the treatment of inherited disease and in the treatment of acquired disease. In the case of inherited diseases, this approach is used to provide genetically engineered hepatocyte precursors or mature hepatocytes differentiated therefrom, which contain DNA encoding a protein or polypeptide which an individual is unable to make correctly. Hepatocyte precursors of the present invention can also be used in the treatment of genetic diseases in which a product (e.g., LDL receptor) normally produced by the liver is not produced or is made in insufficient quantities. Here, hepatocyte precursors transduced with a DNA encoding the missing or inadequately produced substance can be used to produce it in sufficient quantities. In this case, at least a portion of the transduced hepatocyte precursors or a portion of their progeny differentiates into mature hepatocytes, which would produce LDL receptors and thus provide a means of preventing or treating familial hypercholesterolemia. This is an inherited disease in which the primary genetic defect is an abnormality in the expression or function of the receptor for low density lipoproteins, leading to elevated levels of serum cholesterol and the premature development of coronary artery disease. The transduced hepatocyte precursors, and the mature hepatocytes differentiated therefrom could be used to produce sufficient quantities of the LDL receptor to overcome the underlying defect. This approach may also be extended to any patient having a predisposition to atherosclerosis due to hyperlipidemia.

There are also acquired diseases for which treatment can be provided through use of genetically engineered hepatocyte precursors. The genetically engineered hepatocyte precursors may also be employed to treat viral hepatitis, particularly hepatitis B or nonA-nonB hepatitis, by gene transfer. For example, a gene encoding an anti-sense gene could be introduced into hepatocyte precursors to inhibit viral replication. In this case, a vector including a structural hepatitis gene in the reverse or opposite orientation would be introduced into hepatocyte precursors, resulting in production in the genetically engineered hepatocyte precursors and any mature hepatocytes differentiated therefrom of an anti-sense gene capable of inactivating the hepatitis virus or its RNA transcripts. Alternatively, the hepatocyte precursors may be transduced with a gene which encodes a protein, such as, for example, α-interferon, which may confer resistance to the hepatitis virus.

Advantages of employing hepatocyte precursors of the present invention include the provision of a model system for the growth of hepatocyte precursors and/or the differentiation of such hepatocyte precursors into mature hepatocytes. Such a model system of hepatocyte precursors has greater growth potential than cultures of mature hepatocytes, and thus is better suited for various studies of liver cells, such as toxicology studies, carcinogenic studies, and vaccine production. Also, because such hepatocyte precursors may be dissociated from liver tissue and then be enriched and expanded, such expanded hepatocyte precursors obtained from one liver may thus be administered therapeutically to a plurality of patients. The administration of such immature cells may also be less likely to stimulate immune rejection than the injection of mature hepatocytes. In addition, mature hepatocytes may have a limited life span and may undergo a limited number of cell divisions, whereas hepatocyte precursors have a greater capacity to generate daughter cells. Thus, the life span of such a system may be significantly prolonged and possibly may be indefinite.

Examples of non-therapeutic uses of hepatocyte precursors include research of liver embryology, liver cell lineages, and differentiation pathways; gene expression studies; mechanisms involved in liver injury and repair; research of inflammatory and infectious diseases of the liver; studies of pathogenetic mechanisms; and studies of mechanisms of liver cell transformation and etiology of liver cancer. Additional therapeutic uses include liver transplantation for patients with liver failure due to alcoholism, infection, congenital liver diseases, etc., gene therapy for liver diseases that are genetically based such as, for example, Wilson's disease, glycogen storage diseases, urea cycle enzyme defects, and Creigler-Najir disease; and the use of such hepatocyte precursors and any lineages of adult cells derived from them in assays for chemotherapy (e.g., for liver cancers), for the production of vaccines for viruses that grow in the liver, and for studies of alcoholic cirrhosis. The hepatocyte precursors cells may also be employed as part of an "artificial liver;" i.e., the hepatocyte precursors may be placed in a container or apparatus, in which the hepatocyte precursors generate a liver lineage and function as a liver outside of the body. The container or apparatus is connected to the circulatory system of a human or animal subject.

In accordance with another aspect of the present invention, there is provided a composition comprising an animal cell population derived from liver. The cell population contains immature cells which are characterized by expression of alpha-fetoprotein or lack of essential expression of alpha-fetoprotein and albumin, and at least a portion of such cells or of the progeny of such cells is capable of differentiating into adult liver cells. The cells have been cultured under conditions which result in expansion of the immature cells. Such immature cells may be obtained from the livers of human or non-human animals hereinabove described. Although the progeny of such immature cells may differentiate into hepatocytes, such immature cells may differentiate into adult liver cells other than hepatocytes, such as bile duct cells, liver endothelial cells, and lipid-containing liver cells known as Ito cells.

Such immature cells derived from liver may be obtained from liver tissue and enriched or expanded under conditions hereinabove described for the enrichment and expansion of the above-described hepatocyte precursors. It is also contemplated that such immature cells may be genetically engineered through techniques such as those hereinabove described, whereby such genetically engineered cells may be administered to an animal or a human subject, in which the genetically engineered cells and/or their differentiated progeny express gene(s) of interest.

It is to be understood, however, that the scope of the present invention is not to be limited to the specific embodiments described above. The invention may be practiced other than as particularly described and still be within the scope of the accompanying claims.

What is claimed is:

1. A method of expanding hepatic precursor cells comprising culturing immature liver cells which contain at least a population of hepatic precursor cells in serum-free culture medium, an extracellular matrix and liver stromal cells such that hepatic precursor cells contained within the cell culture are expanded.

2. The method of claim 1 wherein the hepatic precursor cells are expanded at least three fold.

3. The method of claim 1 wherein the extracellular matrix is formed from a material selected from the group consisting of collagen, fibronectin, laminin, proteoglycan and combinations thereof.

4. The method of claim 5 wherein the collagen is Type IV.

5. The method of claim 1 wherein the liver stromal cells are selected from the group consisting of embryonic liver stromal cells and fetal liver stromal cells.

6. The method of claim 1 wherein the culture further includes a growth factor.

7. A method of obtaining hepatic precursor cells comprising:
   (a) culturing immature liver cells which contain at least a population of hepatic precursor cells in serum-free culture medium, an extracellular matrix and liver stromal cells such that hepatic precursor cells contained within the cell culture are expanded; and
   (b) separating the expanded hepatic precursor cells from the culture medium so as to obtain hepatic precursor cells.

8. The method of claim 7 wherein the hepatic precursor cells are expanded at least three fold.

9. The method of claim 7 wherein the extracellular matrix is formed from a material selected from the group consisting of collagen, fibronectin, laminin and combinations thereof.

10. The method of claim 7 wherein the collagen is Type IV.

11. The method of claim 7 wherein the liver stromal cells are selected from the group consisting of embryonic liver stromal cells and fetal liver stromal cells.

12. The method of claim 7 wherein the culture further includes a growth factor.

13. A method of obtaining hepatic precursor cells comprising:
   (a) culturing immature liver cells which contain at least a population of hepatic precursor cells in serum-free culture medium, an extracellular matrix, at least one growth factor, and liver stromal cells such that hepatic precursor cells contained within the cell culture are expanded; and
   (b) separating the expanded hepatic precursor cells from the culture medium so as to obtain hepatic precursor cells.

* * * * *